United States Patent
Degeeter

(10) Patent No.: US 9,526,792 B1
(45) Date of Patent: Dec. 27, 2016

(54) COMPOSITION AND METHOD FOR PRODUCING AN EDIBLE BASE PRODUCT

(71) Applicant: NBDD, Inc., San Francisco, CA (US)

(72) Inventor: Doug Degeeter, San Francisco, CA (US)

(73) Assignee: NBDD, Inc., San Francisco, CA (US)

(*) Notice: Subject to any disclaimer, the term of this patent is extended or adjusted under 35 U.S.C. 154(b) by 0 days.

(21) Appl. No.: 14/927,356

(22) Filed: Oct. 29, 2015

(51) Int. Cl.
| | |
|---|---|
| *A01N 65/00* | (2009.01) |
| *A61K 47/46* | (2006.01) |
| *A61K 36/185* | (2006.01) |
| *A61K 31/352* | (2006.01) |
| *A61K 47/36* | (2006.01) |
| *A61K 47/24* | (2006.01) |
| *A61K 9/00* | (2006.01) |

(52) U.S. Cl.
CPC ............ *A61K 47/46* (2013.01); *A61K 9/0053* (2013.01); *A61K 31/352* (2013.01); *A61K 36/185* (2013.01); *A61K 47/24* (2013.01); *A61K 47/36* (2013.01)

(58) Field of Classification Search
CPC ...................................... A61K 36/00
USPC ......................................................... 424/725
See application file for complete search history.

(56) References Cited

FOREIGN PATENT DOCUMENTS

CN          103355726 A     * 10/2013

* cited by examiner

*Primary Examiner* — Michael Meller
(74) *Attorney, Agent, or Firm* — Temmerman Law Office; Mathew J. Temmerman

(57) ABSTRACT

A composition and method for producing an edible base product, the composition comprising a cannabis concentrate containing at least one cannabinoid, a starch concentrate containing tapioca maltodextrin, a rice concentrate, and a lipid concentrate containing lecithin. The method of producing the composition comprises sheering the ingredients at a proper temperature in a dry environment. Preferably, the rice concentrate acts as a natural desiccate and silicate and also an anti-caking agent. The lecithin is added to the powdered cannabis concentrate to enhance the absorption of THC into the blood stream of the individuals. The preferred method transforms the cannabis concentrates into an easily manageable and edible base product useable for a wide variety of medicinal and culinary applications.

5 Claims, No Drawings

COMPOSITION AND METHOD FOR PRODUCING AN EDIBLE BASE PRODUCT

BACKGROUND OF THE DISCLOSURE

Technical Field of the Disclosure

The present embodiment relates in general to edible compositions. More specifically, the present disclosure relates to a composition incorporating cannabis concentrates that are employed as an edible base product for use in a wide variety of medicinal and culinary applications.

Description of the Related Art

Cannabis concentrates are the extracted resins obtained from green leafy marijuana or cannabis containing cannabinoids including tetrahydrocannabinol (THC), cannabidiol (CBD), CBN, CBS, THCV, CBG and other major and minor phytocannabinoids. Resinous cannabis extracts include, but are not limited to BHO, wax, cannabutter, and other fat based cannabis infusions, which are extremely potent cannabis concentrates. These resinous cannabis concentrates are popularly consumed for dabbing and other vaporization methods. Concentrated cannabis resins have traditionally been difficult to work with due to their high viscosity level. At room temperature such resins have the consistency of tree sap or tar and in use can be burdensomely sticky. When resinous cannabis concentrates are heated they become a very thick extremely, sticky substance. By converting concentrated cannabis resins and fat based infusions into powdered form they become not only readily available for ingestion, but can be easily stored and readily available for use with little hassle or inconvenience in measuring out the amount needed from the master batch. The powdered form is adaptable to provide better consistency in the distribution of these cannabis concentrates when applied to edible and sublingual preparations. It also aids in the accurate application of THC to a preparation to obtain a specified volume of THC per portioned batch of the preparation.

Current cannabis compositions developed for edible uses are not ready to use directly from (the freezer) cold storage without thawing. Some cannabis compositions currently available cannot be used for sub-lingual ingestion and do not enhance the absorption of THC into the blood stream of individuals faster than existing ingested edibles. Some of the traditional cannabis compositions contain flour or gluten which consume more total cannabinoids during the cooking process. Furthermore, certain conventional cannabis compositions can cause the production of botulism if improperly stored or in some cases during normal storage when oil infusions are involved.

Given the forgoing, there is a need for an easily produced powdered cannabis product that can be employed as an edible base product for use in a wide variety of medicinal and culinary applications. For purposes of this process, tapioca maltodextrin is used as a medium to produce powdered cannabis concentrates to make them easily ingestible. Tapioca maltodextrin is a light weight bulking agent derived from tapioca starch and when it is mixed with fat, it has the ability to absorb it and transform the fat into a powder like substance. Tapioca maltodextrin is traditionally used to bulk up fats or to thicken fats in commercial food production. When tapioca maltodextrin used in high enough amounts it drastically alters the texture of fats.

In some current uses, the tapioca maltodextrin is mixed with flavored oils such as olive oil, walnut oil or almond oil to create flavored oil based powders. However, such approaches alter the properties of THC and fail to produce the consistency required for culinary and medical applications.

Cannabis compositions can be mixed with flavoring products or oils for culinary applications. However, this process requires cooking which is a time consuming process; and often when the compositions are mixed with other flavoring products or oils their shelf-life is drastically reduced.

Therefore, there is a need for a powdered cannabis composition that is employed as an edible base product useable for a wide variety of medicinal and culinary applications. Such a composition would include tapioca maltodextrin that is mixed with the concentrated resinous secretions of the cannabis plant in a controlled manner to create a potent powdered form of cannabis concentrate without altering the properties of the cannabinoids including THC, CBD, CBN, CBC, THCV, CBG and other cannabinoids present. Such a needed method would provide an edible powdered cannabis product with a stable shelf-life, ready-to-use directly from the freezer with no need for thawing. This composition would be mixed with other food products in a high speed sheering device, without the need for cooking. Such a method would provide an edible powdered cannabis which is free from potential problems like botulism while being stored. This method would also provide an edible powdered cannabis which enhances the absorption of cannabinoids into the blood stream faster than existing ingested edibles. Finally, this composition is suitable for use as a sub-lingual ingestion method.

SUMMARY OF THE DISCLOSURE

To minimize the limitations found in the prior art, and to minimize other limitations that will be apparent upon the reading of the specification, the preferred embodiment of the present invention provides a composition incorporating cannabis concentrates that are employed as an edible base product useable for a wide variety of medicinal and culinary applications. The composition comprises a cannabis concentrate containing at least one cannabinoid compound, a starch concentrate containing tapioca maltodextrin, a rice concentrate, and a lipid concentrate containing lecithin. The composition was prepared in a high speed sheering device by sheering the ingredients at proper temperature in a dry environment. The at least one cannabinoid compound is selected from the group consisting of cannabinol, tetrahydrocannabinol (THC), cannabidiol (CBD), Tetrahydrocannabinol acid, cannabidiol acid, tetrahydrocannabivarin, cannabidivarin, dronabinol, amandamide, nabilone, and combinations thereof. The tapioca maltodextrin is a medium used to produce powdered cannabis concentrate for easy ingestion. The rice concentrate acts as a natural silicate, desiccate and an anti-caking agent. Preferably, the lecithin is added to the powdered cannabis concentrate to enhance the absorption of THC into the blood stream of the individuals while consumption.

The present invention also contemplates a method for producing an edible base product that comprises of shearing a 1:1:1 ratio of a cannabis concentrate by weight containing at least one cannabinoid compound, adding a starch concentrate by weight containing tapioca maltodextrin, adding lipid concentrate containing lecithin and 2% of a rice concentrate by weight, adding and sheering the total ingredients in high speed sheering device to obtain an edible composition.

Unless noted otherwise, all percentages recited in the specification and accompanying claims refer to a weight percentage.

A first objective of the present invention is to provide a composition containing powdered cannabis concentrates that are employed as an edible base product useable for a wide variety of medicinal and culinary applications.

A second objective of the present invention is to provide an edible powdered cannabis concentrates with a stable shelf-life, ready-to-use directly from the freezer with no need for thawing.

A third objective of the present invention is to provide an edible powdered cannabis concentrates that enhances the absorption of THC into the blood stream of individuals faster than existing ingested edibles.

A fourth objective of the present invention is to provide an edible powdered cannabis concentrates which is free from potential problems such as botulism while being stored.

Another objective of the present invention is to provide an edible powdered cannabis concentrates that is suitable for use as a sub-lingual ingestion method.

Another objective of the present invention is to provide a composition that is used as an easy and accurate means for controlling dosage amounts for cannabinoids concentrated for individuals to treat medical conditions and symptoms.

These and other advantages and features of the present invention are described with specificity so as to make the present invention understandable to one of ordinary skill in the art.

DETAILED DESCRIPTION OF THE DISCLOSURE

In the following discussion that addresses a number of embodiments and applications of the present invention in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

The present invention comprises edible compositions and methodology for forming edible compositions. The base composition encompassed by the present invention comprises a cannabis concentrate and a starch concentrate containing tapioca maltodextrin. In addition, the invention relates to the process for providing such "ready-for-use" compositions and the improved food products prepared from the co-processed compositions. The composition further comprises a rice concentrate and a lipid concentrate containing lecithin. Preferably, the rice concentrate is Nu-Flow® rice bran concentrate from Ribus, Inc.

The cannabis concentrate comprises at least one cannabinoid compound. The at least one cannabinoid compound is selected from the group consisting of cannabinol, tetrahydrocannabinol (THC), cannabidiol (CBD), Tetrahydrocannabinol acid, cannabidiol acid, tetrahydrocannabivarin, cannabidivarin, dronabinol, amandamide, nabilone, and combinations thereof. The cannabis concentrate is present in the composition in an amount of about 33% by weight. The cannabis concentrate is extracted from resinous secretions of cannabis plant.

In one embodiment, the cannabis concentrate of the present invention can be used to create various cannabis products. Cannabis products include: canna-butter, solvent reduced oils such as hash oils and other THC infused oils as well as any other fat soluble resinous cannabis secretions.

In one embodiment, the starch concentrates can be derived from a variety of sources including, but not limited to, cereal, tuber, legumes, fruits and vegetable starches. The starch may be modified and/or unmodified and those of skill in the art will understand how to select from one or more of the starches that may be used in the present invention. For example, the starch concentrates is not limited to tapioca maltodextrin and may include corn, waxy maize, sweet potato, potato, canna, arrowroot, sorghum, waxy sorghum, waxy rice, sago, rice, etc., as well as mixtures thereof. The starch concentrate is present in the composition in an amount of about 33% by weight.

In one embodiment of the present invention, the starch concentrate contains tapioca maltodextrin. The maltodextrin is preferably a low DE type, typically less than 20 and is preferably a 10 DE maltodextrin. The tapioca has a unique property of absorbing its own weight in fat. It is believed that the combination of the cannabis concentrate and tapioca maltodextrin produce a powdered form of the cannabis concentrate to make the cannabis concentrate easily ingestible. The combination of the cannabis concentrate and tapioca maltodextrin allows an individual to make the composition into portions of desirable intake amounts. The powdered form of the cannabis concentrate and tapioca maltodextrin can be stored and readily available for use with little hassle or inconvenience in measuring out the amount needed from the master batch.

In one embodiment, the cannabis concentrate is extracted from resinous secretions of cannabis plant. A decarboxylation step may be carried out prior to or after extraction using a solvent. The cannabinoids exist in two forms, as acids and in neutral (decarboxylated) forms. The biologically active forms for human consumption are the neutral forms. The decarboxylation of cannabinoid acid is usually achieved by thorough drying of the plant material followed by heating it, often by either combustion, vaporization, or heating or baking in an oven. Decarboxylation of cannabinoid acids is a function of time and temperature, thus at higher temperatures a shorter period of time will be taken for complete decarboxylation of a given amount of cannabinoid acid. The tapioca maltodextrin is added to concentrated resinous secretions of the cannabis plant in a controlled manner to create a very potent powdered form of the cannabis concentrate without altering the properties of THC and the other cannabinoids. The rice concentrate is applied to increase the flow of the composition and reduce caking due to atmosphere moisture. Preferably, lecithin is added to the cannabis concentrates during the decarboxylation process to enhance the absorption of THC through the liver.

The rice concentrate (preferably NU-Flow® by RIBUS, Inc. of St. Louis, Mo.) is present in the composition in an amount of about 2% by weight (total weight by volume, not baker's percentage), and acts as a natural desiccate and silicate to help keep the product dry and an anti-caking agent. The rice concentrate may be added to the powdered cannabis to aid in the commercial production, storage and packaging of the powdered cannabis. The rice concentrate is a food product that replaces the anti-caking agent $SiO_2$ tri-calcium phosphate, and meets organic labeling guidelines.

The lecithin is adaptable to bind with the THC molecules during the decarboxylation process and enhance the absorption rate of THC during consumption. The lecithin is present in the composition in an amount of about 33% by weight. The lipid concentrate including, but not limited to lecithin, sunflower lecithin, soy lecithin, egg lecithin, peanut lecithin, sesame lecithin, canola lecithin, and combinations thereof.

In one embodiment, the invention provides a method for producing an edible base product which comprises
- a) adding 100 gr of a cannabis concentrate by weight containing at least one cannabinoid compound;
- b) adding 100 gr of a starch concentrate by weight containing tapioca maltodextrin;
- c) adding 2% of a rice concentrate by weight;
- d) adding 100 gr of a lipid concentrate containing lecithin; and
- e) sheering and blending the total ingredients of steps (a) to (d) in a high speed sheering device to obtain an edible composition. EXAMPLES The following examples illustrate, but do not limit, the present invention. Unless otherwise indicated, all parts and percentages are by weight.

Example 1

The following example provides suitable ranges of ingredients for one embodiment of the present invention. In this embodiment, the concentrated form of the product is presented in the following Table 1.

The concentrated form of the composition was prepared from the following ingredients.

TABLE 1

| Ingredients | Amount (wt/wt) |
| --- | --- |
| Cannabis concentrates | 100 gr |
| Tapioca maltodextrin | 100 gr |
| Nu-Flow ® | 6 gr |
| Lecithin | 100 gr |
| Total | 306 gr |

All percentages are by weight of the composition.

The composition was prepared in a high speed sheering device by sheering the ingredients using the method described earlier in this specification at proper temperature in a dry environment.

Example 2

The following example provides suitable ranges of ingredients for one embodiment of the present invention. In this embodiment, the consumption form (intake by the individuals) of the product is presented in the following Table 2.

The consumption form of the composition was prepared from the following ingredients.

TABLE 2

| Ingredients | Amount (wt/wt) |
| --- | --- |
| Cannabis concentrates | 1 gr |
| Tapioca maltodextrin | 100 gr |
| Nu-Flow ® | 2.6 gr |
| Lecithin | 20 gr |
| Total | 123.6 gr |

All percentages are by weight of the composition.

The composition was prepared in a high speed sheering device by sheering the ingredients using the method described earlier in this specification at proper temperature in a dry environment.

Example 3

The following example provides suitable ranges of ingredients for one embodiment of the present invention. In this embodiment, the additive form (used as additive for other food products) of the product is presented in the following Table 3.

The additive form of the composition was prepared from the following ingredients.

TABLE 3

| Ingredients | Amount (wt/wt) |
| --- | --- |
| Cannabis concentrates | 50 gr |
| Tapioca maltodextrin | 100 gr |
| Nu-Flow ® | 1 gr |
| Lecithin | 50 gr |
| Total | 204 gr |

All percentages are by weight of the composition.

The composition was prepared in a high speed sheering device by sheering the ingredients using the method described earlier in this specification at proper temperature in a dry environment.

The above listed ingredients comprise less fat than prior art compositions, meaning that more fatty food products can be mixed with the composition for flavoring. For instance, natural organic oils for chocolate manufacturing are good fats to add because they are essential oils having a stable shelf-life. The other food products are mixed with the composition by sheering at high speed in a sheering device without the need for cooking. For example, dry caramel, freeze dried pineapple, and other suitable ingredients which are in freeze dried or moisture free form may be blended with the composition. The property of the composition may vary with the property of additional food based additives added to the composition.

This composition is used as an easy and accurate means for controlling dosage amounts for THC and other cannabinoids concentrated for persons to treat medical conditions and symptoms. The composition is suitable for use as a sublingual ingestion method. This composition enhances the absorption of THC cannabinoids into the blood stream of the individuals 2 to 3 times faster than existing ingested edibles. The edible powdered cannabis is free from potential problems like botulism while being stored. The composition may be used in a wide variety of commercial food production applications, i.e. salad dressings, cake mixes, flavorings for chips and nuts, instant sauces, etc. The composition has a stable shelf-life, ready-to-use directly from the freezer without thawing, i.e., it is easy to portion and scale directly from the freezer. The frozen powdered cannabis concentrates minimize the loss of the product while handling while pure form cannabis concentrates stick to virtually everything with the exception of silicon at. Individuals having health issues and dietary restriction for using traditional forms of cannabis edibles can safely use the present composition in a desirable amount.

It will also be apparent that various modifications and changes can be made both in the processing and in the relative amounts of the preferred ingredients to prepare food products without departing from the scope of the invention set forth in the claims. All such modifications or changes coming within the terms of the claims are intended to be included in the claims. Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

What is claimed is:

1. A method for producing an edible base product of cannabis consisting essentially of:
    a) adding about 33% of a cannabis concentrate by weight containing at least one cannabinoid compound;
    b) adding about 33% of maltodextrin by weight;
    c) adding about 2% of a rice concentrate by weight; and
    d) sheering and blending the total ingredients of steps (a) to (c) to obtain the edible base product of cannabis.

2. The method of claim 1, wherein the cannabis concentrate is extracted from resin of cannabis.

3. The method of claim 1, wherein the at least one cannabinoid compound is selected from the group consisting of cannabinol, tetrahydrocannabinol, cannabidiol, tetrahydrocannabinol acid, cannabidiol acid, tetrahydrocannabivarin, cannabidivarin, dronabinol, amandamide, nabilone, and combinations thereof.

4. The method of claim 1, wherein the maltodextrin is tapioca maltodextrin.

5. The method of claim 1, wherein the rice concentrate acts as a natural silicate, desiccate and an anti-caking agent.

* * * * *

UNITED STATES PATENT AND TRADEMARK OFFICE
CERTIFICATE OF CORRECTION

| | | |
|---|---|---|
| PATENT NO. | : 9,526,792 B1 | Page 1 of 1 |
| APPLICATION NO. | : 14/927356 | |
| DATED | : December 27, 2016 | |
| INVENTOR(S) | : Doug DeGeeter | |

It is certified that error appears in the above-identified patent and that said Letters Patent is hereby corrected as shown below:

On the Title Page

Item (12): should read DeGeeter

Item (72): Change "Degeeter" to "DeGeeter"

In the Claims

Column 7, Line 18: Change "sheering" to "shearing"

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*